United States Patent [19]

Sun et al.

[11] Patent Number: 5,414,049

[45] Date of Patent: May 9, 1995

[54] NON-OXIDIZING POLYMERIC MEDICAL IMPLANT

[75] Inventors: Deh-Chuan Sun, Rockaway; Casper F. Stark, Pompton Lakes, both of N.J.

[73] Assignee: Howmedica Inc., New York, N.Y.

[21] Appl. No.: 70,074

[22] Filed: Jun. 1, 1993

[51] Int. Cl.⁶ .................................................. C08F 8/00
[52] U.S. Cl. .................................. 525/333.7; 422/22; 422/23
[58] Field of Search .................. 422/22, 23; 525/333.7, 525/24

[56] References Cited

U.S. PATENT DOCUMENTS

| | | | |
|---|---|---|---|
| 3,297,641 | 1/1967 | Werber et al. | 525/333.7 |
| 3,352,818 | 11/1967 | Meyer et al. | 525/333.7 |
| 3,758,273 | 9/1973 | Johnston et al. | 422/23 |
| 5,037,928 | 8/1991 | Li et al. | 526/352 |
| 5,153,039 | 10/1992 | Porter et al. | 428/36 |
| 5,160,464 | 11/1992 | Ward et al. | 526/348.1 |

FOREIGN PATENT DOCUMENTS

0177552 5/1992 European Pat. Off. .
2180815 4/1987 United Kingdom .

OTHER PUBLICATIONS

"Polypropylene Degradation by 2-Irradiation in Air" American Chemical Society, 1985, pp. 359–371.

"Radiation Effects on Polymers" American Chemical Society, 1991 (from symposium of Aug. 26–31, 1990) pp. 89–92.

"Radical Migration as an Elementary Process in Degradation" in Pure & Applied Chem., vol. 55, No. 10, pp. 1595–1601, 1983.

"Combined Chemical and Mechanical Effects on Free Radicals in UHMWPE Joints During Implantation", Journal of Biomedical-Materials Research, vol. 25, pp. 1005–1017, 1991.

*Primary Examiner*—Joseph L. Schofer
*Assistant Examiner*—Tom Weber
*Attorney, Agent, or Firm*—Peter C. Richardson; Lawrence C. Akers; Raymond W. Augustin

[57] ABSTRACT

A medical implant made of polymeric material having an increased oxidation resistance is formed by a method including the steps of placing a resin powder in a sealed container. A substantial portion of the oxygen is removed from the sealed container by either a vacuum, an oxygen absorbent or by flushing with inert gas. The container is then repressurized with a gas such as nitrogen, argon, helium or neon so that long term storage may be possible. On use, the resin is transferred to a forming device which both melts and forms the resin in an oxygen reduced atmosphere to produce a polymeric raw material such as a rod or bar stock. The medical implant is then formed from this raw material annealed and sealed in an airtight package in an oxygen reduced atmosphere. The implant is then radiation sterilized and thereafter annealed in the package for a predetermined time and temperature sufficient to form cross-links between any free radicals in neighboring polymeric chains.

41 Claims, No Drawings

NON-OXIDIZING POLYMERIC MEDICAL IMPLANT

BACKGROUND OF THE INVENTION

2. Field of the Invention

This invention relates to medical implants formed of a polymeric material such as ultra-high molecular weight polyethylene, with superior oxidation resistance upon irradiation and a method for making the same.

2. Description of the Prior Art

Various polymer systems have been used for the preparation of artificial prostheses for biomedical use, particularly orthopedic applications. Among them, ultra-high molecular weight polyethylene is widely used for articulation surfaces in artificial knee and hip replacements. Ultra-high molecular weight polyethylene (UHMWPE) has been defined as those linear polyethylenes which have a relative viscosity of 2.3 or greater at a solution concentration of 0.05% at 135° C. in decahydronaphthalene. The nominal weight—average molecular weight is at least 400,000 and up to 10,000,000 and usually from three to six million. The manufacturing process begins with the polymer being supplied as fine powder which is consolidated into various forms, such as rods and slabs, using ram extrusion or compression molding. Afterwards, the consolidated rods or slabs are machined into the final shape of the orthopedic implant components. Alternatively, the component can be produced by compression molding of the UHMWPE resin powder.

All components must then go through a sterilization procedure prior to use, but usually after being packaged. There exists several sterilization methods which can be utilized for medical applications, such as the use of ethylene oxide, heat, or radiation. However, applying heat to a packaged polymeric medical product can destroy either the integrity of the packaging material (particularly the seal, which prevents bacteria from going into the package after the sterilization step) or the product itself.

Because ethylene oxide may adversely impact environmental and employee safety, gamma ray, x-ray or electron beam radiation has been utilized as a preferred means of sterilization. These types of radiation use a high energy beam to kill bacteria, viruses, or other microbial species contained in the packaged medical products, achieving the goal of product sterility.

However, it has been recognized that regardless of the radiation type, the high energy beam causes generation of free radicals in polymers during radiation. It has also been recognized that the amount of free radicals generated is dependent upon the radiation dose received by the polymers and that the distribution of free radicals in the polymeric implant depends upon the geometry of the component, the type of polymer, the dose rate, and the type of radiation beam. The generation of free radicals can be described by the following reaction (which uses polyolefin and gamma ray irradiation for illustration):

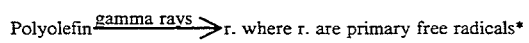

Polyolefin $\xrightarrow{\text{gamma rays}}$ r. where r. are primary free radicals* (1)

*(through C—C chain scission or C—H scission)

Depending whether or not oxygen is present, primary free radicals r. will react with oxygen and the polymer according to the following reactions as described in "Radiation Effects on Polymers", edited by Roger L. Clough and Shalaby W. Shalaby, published by American Chemical Society, Washington, D.C., 1991.

In the presence of oxygen $$r. \xrightarrow{O_2} rO_2. \quad (2)$$

$$rO_2. + \text{polyolefin} \longrightarrow rOOH + P. \quad (3)$$

$$P. + O_2 \longrightarrow PO_2. \quad (4)$$

$$PO_2. + \text{polyolefin} \longrightarrow POOH + P. \xrightarrow{O_2} PO_2. \quad (5)$$

$$rO_2., PO_2. \longrightarrow \text{Some chain scission products} \quad (6)$$

$$rOOH, POOH \xrightarrow{\text{room temperature}} \text{free radicals, rOH, POH} \quad (7)$$

$$P. + PO_2. \longrightarrow POOP(\text{ester cross-links}) \quad (8)$$

$$2P. \longrightarrow P—P(C—C \text{ cross links}) \quad (9)$$

In radiation in air, primary free radicals r. will react with oxygen to form peroxyl free radicals $rO_2.$, which then react with polyolefin (such as UHMWPE) to start the oxidative chain scission reactions (reactions 2 through 6). Through these reactions, material properties of the plastic, such as molecular weight, tensile, and wear properties, are degraded.

Recently, it was found that the hydroperoxides (rOOH and POOH) formed in reactions 3 and 5 will slowly break down as shown in reaction 7 to initiate post-radiation degradation. Reactions 8 and 9 represent termination steps of free radicals to form ester or carbon-carbon cross-links. Depending on the type of polymer, the extent of reaction 8 and 9 in relation to reactions 2 through 7 may vary. For irradiated UHMWPE, a value of 0.3 for the ratio of chain scission to cross-linking has been obtained, indicating that even though cross-linking is a dominant mechanism, a significant amount of chain scission occurs in irradiated polyethylene.

By applying radiation in an inert atmosphere, since there is no oxidant present, the primary free radicals r. or secondary free radicals P. can only react with other neighboring free radicals to form carbon-carbon cross-links, according to reactions 10 through 12 below. If all the free radicals react through reactions 10 through 12, there will be no chain scission and there will be no molecular weight degradation. Furthermore, the extent of cross-linking is increased over the original polymer prior to irradiation. On the other hand, if not all the free radicals formed are combined through reactions 10, 11 and 12, then some free radicals will remain in the plastic component.

In an Inert Atmosphere $$r. + \text{polyolefin} \longrightarrow P. \quad (10)$$

$$2r. \longrightarrow r—r(C—C \text{ cross linking}) \quad (11)$$

$$2P. \longrightarrow P—P(C—C \text{ cross linking}) \quad (12)$$

It is recognized that the fewer the free radicals, the better the polymer retains its physical properties over time. The greater the number of free radicals, the greater the degree of molecular weight and polymer property degradation will occur. Applicant has discovered that the extent of completion of free radical cross-linking reactions is dependent on the reaction rates and the time period given for reaction to occur.

Several prior art patents attempt to provide methods which enhance UHMWPE physical properties. European Patent Application 0 177 522 B1 discloses UHMWPE powders being heated and compressed into a homogeneously melted crystallized morphology with no grain memory of the UHMWPE powder particles and with enhanced modulus and strength. U.S. Pat. No. 5,037,928 discloses a prescribed heating and cooling process for preparing a UHMWPE exhibiting a combination of properties including a creep resistance of less than 1% (under exposure to a temperature of 23° C. and a relative humidity of 50% for 24 hours under a compression of 1000 psi) without sacrificing tensile and flexural properties. U.K. Patent Application GB 2 180 815 A discloses a packaging method where a medical device which is sealed in a sterile bag, after radiation/sterilization, is hermetically sealed in a wrapping member of oxygen-impermeable material together with a deoxidizing agent for prevention of post-irradiation oxidation.

U.S. Pat. No. 5,153,039 relates to a high density polyethylene article with oxygen barrier properties. U.S. Pat. No. 5,160,464 relates to a vacuum polymer irradiation process.

SUMMARY OF THE INVENTION

The present invention relates to a method for providing a polymeric material, such as UHMWPE, with superior oxidation resistance upon irradiation. For the purpose of illustration, UHMWPE will be used as an example to describe the invention. However, all the theories and processes described hereafter should also apply to other polymeric materials such as polypropylene, high density polyethylene, polyester, nylon, polyurethane and poly(methylmethacrylate) unless otherwise stated.

As stated above, while UHMWPE polymer is very stable and has very good resistance to aggressive media except for strong oxidizing acids. Upon sterilization radiation, free radicals are formed which cause UHMWPE to become activated for chemical reactions and physical changes. Possible chemical reactions include reacting with oxygen, water, body fluids, and other chemical compounds while physical changes include density, crystallinity, color, and other physical properties. In the present invention a new sterilization radiation process greatly reduces the adverse effects caused by a conventional radiation process. Furthermore, this new sterilization process does not employ stabilizers, antioxidants, or any other chemical compounds which may have potential adverse effects in biomedical or orthopedic applications.

In the sterilization process of the present invention, a polymeric orthopedic implant component to be sterilized by radiation does not contain oxidants, such as oxygen or water (or moisture), or free radicals. This may be accomplished by obtaining a raw material for the implant manufactured under a special process as described herein and forming a part of the invention.

The finished polymeric orthopedic component is then sealed in an oxidant-free atmosphere. This oxidant-free atmosphere is maintained during radiation. The radiated polymeric component is then subjected to a heat treatment to cross-link all the free radicals within themselves. During this treatment, the condition of oxidant-free atmosphere is maintained. The irradiated, heat treated plastic component is now ready to use. Exposure to oxygen or moisture will not cause oxidation. The oxidation resistance to any oxidizing agent is similar to that of the unirradiated virgin polymer.

It is therefore an object of the invention to provide a polymeric orthopedic implant having superior oxidation resistance after irradiation.

It is still another object of the invention to provide a method for manufacturing such an implant from the resin powder thereof through the final sterilization step so that the implant may thereafter be exposed to air without degradation due to oxidation.

These and other objects are achieved by a method for producing a polymeric medical implant including the steps of placing the polymeric resin in a sealed container and removing a substantial portion of the oxygen from the container. After a predetermined time, the container is repressurized with an inert gas such as nitrogen, argon, helium or neon. The resin is thereafter transferred to a forming device which normally melts and forms the resin in an oxygen reduced atmosphere to produce a polymeric raw material. The polymeric raw material, such as UHMWPE is then machined to an implant such as a tibial tray or a liner for an acetabular cup. The finished part is then sealed into a package in an oxygen reduced atmosphere. The package is of an air-tight nature to prevent oxygen or moisture from entering after the package is sealed. The then packaged implant is radiation sterilized and then heat treated for the predetermined time and temperature sufficient to form cross-links between free radicals of the neighboring polymeric chains. This prevents further oxidation once the implant is removed from the package.

In general, the implant is heated for at least 48 hours at a temperature of about 37° C. to about 70° C. and preferably for 144 hours at 50° C.

DESCRIPTION OF THE PREFERRED EMBODIMENT

In the preferred method, a raw polymeric material such as UHMWPE is obtained by, for example, ram extrusion, compression molding, or other forming processes. These methods use virgin polymer powder as a starting material. However, virgin polymer resin powder may contain air or moisture, which may exist in the resin micro-structure or simply deposited on the resin surfaces. If air or moisture is not removed from resin powder prior to the forming process, it can be trapped in the plastic matrix after forming and can not escape. This is true even with the use of vacuum or gas flushing techniques. During the sterilization radiation process, the trapped air or moisture or both will react with free radicals generated in the plastic to cause oxidation. The trapped moisture can also absorb radiation energy and dissociate into oxygen and hydroxyl free radicals which will also react with the plastic to cause oxidation. Therefore, by removing air and moisture prior to the forming process, oxidation during sterilization radiation can be avoided.

The preferred method for eliminating air and moisture is to apply a vacuum of less than 3" of mercury (76 torr) to the polymer resin for a prescribed time to reduce the levels of air and moisture to a minimal or acceptable value. The level for oxygen is preferably 0.5% (volume by volume and no more than 1%). The moisture level is preferably 10% of relative humidity (and no more than 20% relative humidity). Then sufficient amounts of deoxidizing agents, such as oxygen absorbents and moisture desiccants, are placed together with the polymer resin in a sealed container to reduce the levels of air and moisture to the minimal or acceptable value. An example of an oxygen absorbent is AGELESS® which is an iron oxide compound and commercially available from Cryovac Division, W. R. Grace & Co., Duncan, S.C. An example of moisture desiccant is silica gel which is commercially available. These materials are placed with the resin in the sealed container for approximately 10 hours. Alternately, or in combination, an inert gas, such as nitrogen, argon, helium or neon is used to flush the container, holding the polymer resin powder, until the levels of air and moisture are reduced to the accepted value. Of course, any combination of the above methods can also be used.

In order to ensure a raw material for an orthopedic implant with no oxygen, not only must the UHMWPE resin powder be free of air and moisture, but the entire forming operation of, for example, ram extrusion, compression molding, or other forming process should be carried out in an inert or low oxygen atmosphere as well. During the forming process, due to high temperature and high pressure applied in the process, UHMWPE polymer chains may be broken to generate free radicals and cross-links. While cross-links generated in the forming process have no adverse effects on material properties, the free radicals produced, as described above, can react with air or other oxidants. Therefore, it is important to maintain the inert atmosphere during the forming process to minimize oxidation.

Any free radicals generated should be eliminated as soon as the forming process is completed by annealing. If the formed UHMWPE contains free radicals and is exposed to air or other oxidants after the forming process, oxidation will occur. The polymer should be annealed at an elevated temperature in an inert atmosphere for a prescribed time. This is because the rate of free radical reactions (reactions 10 through 12) increase with increasing temperature, according to the following general expressions:

$$\frac{dr\cdot}{dt} = k_1 [r\cdot] \text{ and } \frac{dP\cdot}{dt} = k_2 [P\cdot] \quad (13)$$

Compared to room temperature, an elevated temperature not only increases the reaction rate constants, $k_1$, and $k_2$, but also helps free radicals r. and P. to migrate in the plastic matrix to meet other neighboring free radicals for cross-linking reactions. In general, the desired elevated temperature is between the room temperature and the melting point of the polymer. For UHMWPE, this temperature range is between about 25° C. and about 140° C. However, the preferred annealing temperature range is from about 37° C. to about 135° C. The preferred time and temperature is 130° C. for 20 hours with the minimum annealing time being about 4 hours (requiring a temperature at the high end of the range). It is to be noted that the higher the temperature used, the shorter the time period needed to combine free radicals. Additionally, due to the high viscosity of an UHMWPE melt, the formed UHMWPE often contains residual (internal) stress caused by incomplete relaxation during the cooling process, which is the last step of the forming process. The annealing process described herein will also help to eliminate or reduce the residual stress. A residual stress contained in a plastic matrix can cause dimensional instability and is in general undesirable.

In applications such as for orthopedic implants, the formed UHMWPE is further machined into desired shapes. In general, the machining is done at room temperature and no damage to the plastic will occur. However, certain machine tools, when operated at a high speed, may generate local heat and cause thermal breakdown of UHMWPE polymer chains. In this case, the above described annealing process may be employed to eliminate any newly formed free radicals prior to packaging.

After machining, the polymeric component is packaged in an air tight package in an oxidant-free atmosphere. Thus, all air and moisture must be removed from the package prior to the sealing step. Machines to accomplish this are commercially available, such as from Orics Industries Inc., College Point, N.Y. which flush the package with a chosen inert gas, vacuum the container, flush the container for the second time, and then heat seal the container with a lid. In general, less than 0.5% (volume by volume) oxygen concentration can be obtained consistently. An example of a suitable oxidant impermeable (air tight) packaging material is polyethylene terephthalate (PET). Other examples of oxidant impermeable packaging material is poly(ethylene vinyl alcohol) and aluminum foil, whose oxygen and water vapor transmission rates are essentially zero. All these materials are commercially available. Several other suitable commercial packaging materials utilize a layer structure to form a composite material with superior oxygen and moisture barrier properties. An example of this type is a layered composite comprised of poly-propylene/poly(ethylene vinyl alcohol)/polypropylene.

In general, the sterilization radiation step for the packaged implant may take a few hours to complete. As described above, it is imperative that during this time period, the transmission of oxidants, such as oxygen and moisture, into the package be kept to a minimal or at an acceptable value to avoid oxidation.

Following sterilization radiation, a heat treatment step should be performed in an inert atmosphere and at an elevated temperature to cause free radicals to form cross-links without oxidation. If proper packaging materials and processes are used and oxidant transmission rates are minimal, then the oxidant-free atmosphere can be maintained in the package and a regular oven with air circulation can be used for heat treatment after sterilization. To absolutely ensure that no oxidants leak into the package, the oven may be operated under a vacuum or purged with an inert gas. In general, if a higher temperature is used, a shorter time period is required to achieve a prescribed level of oxidation resistance and cross-linking. In many cases, the relationship between the reaction temperature and the reaction rate follows the well-known Arrhennius equation:

$$k_1, \text{ or } k_2 = A^* \exp(\Delta H/T) \quad (14)$$

where $k_1$ and $k_2$ are reaction rate constants from reactions 13 and 14 A is a reaction dependent constant $\Delta H$ is activation energy of reaction T is absolute temperature (K)

However, the temperature should not exceed the distortion temperature of either the packaging material or the plastic components. For UHMWPE, the temperature range is between about 25° C. and about 140° C. However, considering the distortion of the packaging material, the preferred temperature is 37° C. to 70° C.

It is very important to ensure that the number of free radicals has been reduced to a minimal or an accepted level by the heat treatment. This is because the presence of an oxidant causes not only the oxidation of pre-existing free radicals, but also the formation of new free radicals via reactions 2 through 7. When the number of free radicals grows, the extent of oxidation and the oxidation rate will increase according to the following equations:

$$\frac{dr\cdot}{dt} = k_3 [r\cdot][O_2] \text{ and } \frac{dP\cdot}{dt} = k_4 [P\cdot][O_2] \quad (15)$$

Where free radicals r. and P. can grow in number in the presence of oxidants and in turn increase the oxidation rates. It is also to be noted that the oxidation reaction rate constants $k_3$ and $k_4$ increase with increasing temperature, similar to $k_1$ and $k_2$. Therefore, to determine if a certain level of residual free radicals is acceptable or not, it is required to evaluate specific material properties after the plastic sample is stored or aged at the application temperature for a time period which is equal to or longer than the time period intended for the application of the plastic component. An alternative to the method to assess the aging effect is to raise the aging temperature of the plastic sample for a shorter time period. This will increase the reaction rate constants $k_3$ and $k_4$ significantly and shorten the aging time. It has been found that an acceptable level of residual free radicals is $1.0 \times 10^{17}$/g for UHMWPE use for orthopedic implants. After heat treatment, the irradiated packaged plastic component is now ready to use. The package can be opened and exposed to air or moisture without causing oxidation. The oxidation resistance of the sterilized plastic component to other oxidants is similar to that of the virgin, unirradiated polymer.

Sample Preparation

A surgical grade UHMWPE rod produced by ram extrusion was machined into samples of desirable shapes. Four sets of samples were prepared using these machined samples by the following methods:

Method A: an UHMWPE sample as machined and unirradiated

Method B: An UHMWPE sample was heat sealed in a glycol-modified polyethylene terephthalate (PETG, made by Eastman Plastics, Inc., Kingsport, Tenn.) blister in air with an aluminum lid of 0.1 mm in thickness. The sealed blister containing the UHMWPE sheet was sterilized by irradiation of gamma-rays in a dose of 2.5 Mrad. The package was then opened and exposed to room air.

Method C: An UHMWPE sample was placed in a PETG blister and heat sealed in dry nitrogen with an aluminum lid of 0.1 mm in thickness by the Orics Vacuum Gas Flush Heat Seal Machine (Model SLS-VGF-100M for modified atmosphere packaging, made by Orics Industries Inc., College Point, N.Y.) which went through the following cycles: i) nitrogen gas (moisture-free) flush for five seconds ii) vacuum to a pressure of equal to or below 3 inches of mercury iii) nitrogen gas flush (moisture-free) for five seconds iv) heat seal The oxygen concentration in the sealed blister was measured by a Mocon Oxygen Analyzer to be 0.325% (volume by volume). The sealed blister containing the UHMWPE sample was sterilized by irradiation of gamma-rays in a dose of 2.5 Mrad. The oxygen concentration in the sealed blister after sterilization radiation was measured to be 0.350%. The package was then opened and exposed to room air.

Method D:

Same as Method C, except that after gamma-ray irradiation, the sealed blister containing the UHMWPE sample was heat treated at 50° C. for 144 hours in an oven, then transferred from the oven to room temperature for cooling. After the package was cooled to room temperature, the oxygen concentration was measured by a Mocon Oxygen Analyzer to be 0.360%. The package was then opened and exposed to room air.

Samples prepared by the above methods were used in the following examples for evaluation.

Example 1

Two sets of 1-mm-thick UHMWPE sheets prepared by Methods A through D above were oven aged in air at 80° C. for 11 and 23 days respectively. After these sheets were cooled in room temperature, a thin film specimen of about 100 microns in thickness was cut from each of the 1-mm-thick aged UHMWPE sheets and placed in an IR window for a standard FTIR (A Nicolet 710 FTIR system was used) transmission run. A total of 32 spectra (scans) were collected and averaged. To determine the extent of oxidation, the IR absorption peaks in the frequency range of between 1660 and 1800 $cm^{-1}$, corresponding to carbonyl (C-O) functional groups, were integrated for the peak area. The peak area is proportional to the amount of oxidized UHMWPE in the specimen. To correct for difference in specimen thickness, the integrated peak area was then normalized to the specimen thickness, by dividing by the area of the 1463 $cm^{-1}$ (methyl) peak which is proportional to the specimen thickness. The obtained ratio was defined as oxidation index. A third set of 1-mm-thick UHMWPE sheets prepared by methods A through D, but without oven aging, were also evaluated by the same FTIR method for comparison. Oxidation indices obtained are shown in Table 1:

TABLE 1

| Sample | Oxidation Index |
| --- | --- |
| Method A/not oven aged | ca. 0. |
| Method A/11 day oven aging | ca. 0. |
| Method A/23 day oven aging | ca. 0. |
| Method B/not oven aged | 0.02 |
| Method B/11 day oven aging | 0.06 |
| Method B/23 day oven aging | 0.11 |
| Method C/not oven aged | 0.01 |
| Method C/11 day oven aging | 0.04 |
| Method C/23 day oven aging | 0.08 |
| Method D/not oven aged | 0.01 |
| Method D/11 day oven aging | 0.01 |
| Method D/23 day oven aging | 0.01 |

From Table 1 results, it can be seen that the unirradiated UHMWPE sample (Method A) was free of oxidation (below the FTIR detectable level), even after 23 days of oven aging in air at 80° C. On the other hand, the UHMWPE sample irradiated in air (Method B) showed considerable oxidation and the extent of oxidation (as indicated by the oxidation index) increased with increasing aging time. After 23 days of oven aging, the oxidation index reached 0.11. For the UHMWPE sample irradiated in nitrogen (Method C), the initial oxidation index before oven aging was 0.01 which was not significant. However, during the oven aging, the oxidation index increased to 0.04 for 11 days and 0.08 for 23 days respectively. The results indicate that while irradiation in an inert atmosphere is an improvement over oxidation in air, the irradiated plastic component will oxidize further over time once it is exposed to air or other oxidants. In contrast, the UHMWPE sample irradiated in nitrogen followed by heat treatment at 50° C. for 144 hours (Method D), showed an initial oxidation index of only 0.01 which did not increase after 11 or 23 days of oven aging, indicating that this sample has superior oxidation resistance than the samples prepared by Method B or C.

Example 2

Two sets of 1-mm-thick UHMWPE sheets prepared by Methods B through D cited in the Sample Preparation were oven aged in air at 80° C. for 11 and 23 days respectively. After these sheets were cooled in room temperature, six tensile specimens with a dumbbell shape according to ASTM D638 (Type IV) were cut from each of the 1-mm-thick aged UHMWPE sheets. A standard tensile test was performed for each specimens at a speed of 2 inches/min. Another set of 1-mm-thick UHMWPE sheets prepared by Methods B through D cited in the Sample Preparation, but without oven aging, were also evaluated by the same tensile test method for comparison. Tensile breaking strength results (average of six tests for each condition) are shown in Table 2:

TABLE 2

| Sample | Tensile Breaking Strength, psi |
| --- | --- |
| Method B/not oven aged | 6510 |
| Method B/11 day oven aging | 5227 |
| Method B/23 day oven aging | 3192 |
| Method C/not oven aged | 6875 |
| Method C/11 day oven aging | 6400 |
| Method C/23 day oven aging | 6004 |
| Method D/not oven aged | 6941 |
| Method D/11 day oven aging | 7113 |
| Method D/23 day oven aging | 6904 |

From Table 2, tensile breaking strength shows the most deterioration for the sample irradiated in air (Method B). The sample irradiated in nitrogen (Method C) shows some improvement over the sample prepared by Method B. However, the decrease in tensile breaking strength upon oven aging still occurs. In contrast, the sample irradiated in nitrogen followed by heat treatment (50° C. for 144 hours, Method D), shows no change in tensile breaking strength, indicating a superior oxidation resistance.

Example 3

Two sets of 1-mm-thick UHMWPE sheets prepared by Methods B and Method D cited in the Sample Preparation were oven aged in air at 80° C. for 11 and 23 days respectively. After these sheets were cooled in room temperature, samples cut from sheets were characterized by a high temperature gel permeation chromatograph (GPC) column for molecular weight distribution. The samples were dissolved in hot trichlorobenzene (TCB). They were then run in the aforementioned solvent at 1.2 ml/min. using a Jordi Gel Mixed Bed Column, 50 cm × 10.0 mm ID., at a column oven temperature of 145° C. on the Waters 150C Chromatograph. The injection size was 250 uL of a 0.1% solution. An antioxidant (N-phenyl-2-naphthylamine) was added to all high temperature GPC samples to prevent polymer deterioration.

Prior to sample runs, the column was calibrated using narrow MW polystyrene standards. Since the samples were only partially soluble in the solvent due to cross-linking, the so-determined molecular weight distribution was for the soluble portion only. To determine the extent of cross-linking (solubility), a two hundred milligram sample cut from sheets were dissolved in 100 cc of 1,2,4-trichlorobenzene. Each sample was then heated to approximately 170° C. with N-phenyl-2-naphthylamine antioxidant added for 6 hours. The samples were then hot filtered at approximately 170° C. using separate preweighed high temperature filters for each sample.

After filtration, the filters were cooled to room temperature and washed individually with dichloromethane. They were then placed in a convection oven at 105° C. for 6 hours to dry and then reweighed. The weight fraction of the undissolved (cross-linked) portion was then determined based upon the initial weight of 200 mg. To determine the low molecular weight fraction present in each sample, the weight fraction of molecular weight below $10^5$ in the soluble portion, determined by GPC, was multiplied by the percent solubility to give weight percent of low molecular weight fraction in each sample. Results are shown in Table 3:

TABLE 3

| Sample | Weight Percent of Soluble Portion Below $10^5$ | Percent Solubility in Solvent | Weight Percent of Entire Sample Below $10^5$ |
| --- | --- | --- | --- |
| Method B/ without oven aging | 28.0 | 98.2 | 27.5 |
| Method B/ 11 day oven aging | 36.2 | 100.0 | 36.2 |
| Method B/ 23 day oven aging | 48.1 | 100.0 | 48.1 |
| Method D/ without oven aging | 22.7 | 80.9 | 18.4 |
| Method D/ 11 day oven aging | 20.5 | 73.6 | 15.1 |
| Method D/ 23 day oven aging | 24.2 | 74.7 | 18.1 |

From Table 3, it can be seen that the sample made by Method D contains more cross-linking (i.e. less soluble) than one made by Method B. Upon oven aging, the low molecular weight fraction (defined as below $10^5$) in the sample made by Method B increases from 0.275 to 0.481 while that of the sample made by Method D remains virtually unchanged at about 0.18 after 23 days of oven aging. The increase in low molecular weight fraction was due to chain scission caused by oxidative reactions. The results indicate that the process of method D can produce an irradiated polymer with a superior oxidation resistance.

Example 4

UHMWPE samples of 0.5 inch cubes prepared by Methods B and Method D cited in the Sample Preparation were evaluated for deformation under load (creep resistance). Testing procedures according to ASTM D 621 (A) (24 hr/23° C./1000 psi/90 min recovery) were used. Results are summarized in Table 4:

TABLE 4

| Sample | Deformation under Load, % |
|---|---|
| Method B | 0.80 |
| Method D | 0.60 |

From Table 4, it is concluded that the sample prepared by Method D, the invention, possesses a superior creep resistance (0.6%) to one prepared by Method B (0.8%).

Example 5

Two 1-mm-thick UHMWPE samples were annealed in a oven filled with air and dry nitrogen (oxygen concentration is below 0.2%) respectively at 130° C. for 20 hours in order to remove residual stress on the samples. After the sheets were cooled to room temperature in the oven, they were removed from the oven and cut into dumbbell shaped tensile specimens (ASTM D 638, Type V) for evaluation. A standard tensile test according to ASTM D 638 was performed at a speed of 2 inches/min for each of six specimens annealed in air and in dry nitrogen respectively. Results are shown in Table 5:

TABLE 5

| Sample | EAB, % | TYS, psi | TBS, psi | Toughness, lbs-in/in$^3$ |
|---|---|---|---|---|
| Air annealed | 414 | 3547 | 6257 | 10,210 |
| Nitrogen annealed | 485 | 3517 | 8917 | 18,960 |

Note:
EAB — elongation at break
TYS — tensile yield strength
TBS — Tensile breaking strength From the above table, it is seen that the sample annealed in nitrogen exhibits a higher elongation at break, a higher tensile breaking strength, and a higher toughness, compared to one annealed in air, while the tensile yield strength is similar between the two samples. The results indicate that the sample annealed in nitrogen is more ductile than the one annealed in air. The loss of ductility in the sample annealed in air is due to oxidative chain scission.

To determine oxidation indices in these two samples, a thin film specimen of ca. 100 microns in thickness was cut from each of the 1-mm-thick annealed UHMWPE sheets and placed in an IR window for a standard FTIR (a Nicolet 710 FTIR system was used) transmission run, using the procedures and calculations employed in the Sample Preparation. Oxidation indices obtained are shown in Table 6.

TABLE 6

| Sample | Oxidation Index |
|---|---|
| Air Annealed | 0.10 |
| Nitrogen Annealed | ca. 0.0 |

From the above results, it is seen that the UHMWPE sample annealed in air after ram extrusion showed significant oxidation due to free radicals generated in the forming process. In contrast, the UHMWPE sample annealed in nitrogen showed no oxidation (below the FTIR detectable level). It is concluded that annealing in nitrogen can prevent the polymer from oxidation and produce a polymer with superior ductility.

While several examples of the present invention have been described, it is obvious that many changes and modifications may be made thereunto, without departing from the spirit and scope of the invention.

We claim:

1. A method for producing a medical implant formed from an olefinic material, the material having improved oxidation resistance comprising the steps of:
   sealing the implant in an oxygen impermeable package in an oxygen reduced non-reactive atmosphere;
   radiation sterilizing said packaged implant; and
   heating said packaged implant for a predetermined time at a temperature of between about 37° C. and the melting point of said olefinic material to form cross-links between free radicals in neighboring polymeric chains.

2. The method for producing an implant set forth in claim 1 wherein said predetermined temperature is between about 37° C. and about 70° C.

3. The method for producing an implant as set forth in claim 2 wherein said predetermined time is at least forty eight hours.

4. The method for producing an implant as set forth in claim 3 wherein said predetermined temperature is 50° C. and said predetermined time is 144 hours.

5. The method for producing an implant as set forth in claim 1 wherein the polymeric material is ultra high molecular weight polyethylene having a molecular weight between 400,000 and 10,000,000.

6. The method for producing an implant as set forth in claim 5 wherein said predetermined temperature is 50° C. and said predetermined time is 144 hours.

7. The method for producing an implant as set forth in claim 1 wherein said radiation sterilization is performed by gamma, x-ray or electron beam radiation.

8. The method as set forth in claim 1 wherein said oxygen reduced atmosphere has no more than 1% oxygen.

9. The method for producing an implant as set forth in claim 8 wherein said oxygen reduced atmosphere is made up of a gas selected from the group consisting of nitrogen, helium, argon, and neon and a combination thereof.

10. The method for producing an implant as set forth in claim 8 wherein said reduced oxygen atmosphere is produced by a vacuum of less than 3 inches of mercury.

11. The method for producing an implant as set forth in claim 8 wherein said sealing in a reduced oxygen atmosphere is produced by first flushing said package with a gas selected from the group consisting of nitrogen, helium, argon and neon and a combination thereof, followed by applying a vacuum of less than 3 inches of mercury to said package, followed by flushing said package with a gas selected from said group and a combination thereof.

12. A method for producing a medical implant made from an olefinic material having a molecular weight of between 400,000 and 10,000,000 comprising the steps of:
   forming the implant from the olefinic material;
   packaging the formed implant in an inert atmosphere;
   radiation sterilizing said packaged implant while maintaining said inert atmosphere; and
   heating said packaged implant while maintaining said inert atmosphere for at least 48 hours at a temperature of about 37° C. to about 70° C.

13. The method for producing an implant as set forth in claim 12 wherein the olefinic material is ultra high molecular weight polyethylene.

14. The method for producing an implant as set forth in claim 12 wherein said predetermined temperature is 50° C. and said predetermined time is 144 hours.

15. The method as set forth in claim 12 wherein said oxygen reduced atmosphere has no more than 1% oxygen.

16. The method for producing an implant as set forth in claim 15 wherein said inert atmosphere is made up of a gas selected from the group consisting of nitrogen, helium, argon, and neon and a combination thereof.

17. The method for producing an implant as set forth in claim 15 wherein said inert atmosphere is produced by a vacuum of less than 3 inches of mercury.

18. The method as set forth in claim 12 wherein said heating step is performed in an inert atmosphere.

19. A method for producing a medical implant from an olefinic material having a molecular weight greater than 400,000 comprising the steps of:
sealing the implant in an oxygen impermeable package in an oxygen reduced atmosphere having an absence of agents which can react with free radicals in the polymeric chain;
radiation sterilizing said packaged implant; and
heating said sealed packaged implant for a predetermined time and temperature sufficient to form cross-links between free radicals in neighboring polymeric chains.

20. The method as set forth in claim 19 wherein said oxygen reduced atmosphere has no more than 1% oxygen.

21. The method for producing an implant as set forth in claim 20 wherein said oxygen reduced atmosphere is made up of a gas selected from the group consisting of nitrogen, helium, argon, and neon and a combination thereof.

22. The method for producing an implant as set forth in claim 20 wherein said oxygen reduced atmosphere is produced by a vacuum of less than 3 inches of mercury.

23. The method for producing an implant as set forth in claim 20 wherein said sealing in said oxygen reduced atmosphere is produced by first flushing said package with a gas selected from the group consisting of nitrogen, helium, argon and neon and a combination thereof, followed by applying a vacuum of less than 3 inches of mercury to said package, followed by flushing said package with a gas selected from said group and a combination thereof.

24. The method for producing an implant as set forth in claim 19 wherein the olefinic material is ultra high molecular weight polyethylene having a molecular weight between 400,000 and 10,000,000.

25. A method for producing a medical implant made from olefinic material having a molecular weight greater than 400,000 comprising the steps of:
sealing the implant in an oxygen impermeable package in an inert atmosphere;
radiation sterilizing said packaged implant; and
heating said packaged implant for at least four hours at a temperature of between 37° C. and the melting point of said olefinic material to form cross-links between free radicals in neighboring polymeric chains.

26. The method as set forth in claim 25 wherein said inert atmosphere has no more than 1% oxygen.

27. The method for producing an implant as set forth in claim 26 wherein said inert atmosphere is made up of a gas selected from the group consisting of nitrogen, helium, argon, and neon and a combination thereof.

28. The method for producing an implant as set forth in claim 26 wherein said inert atmosphere is produced by a vacuum of less than 3 inches of mercury.

29. The method for producing an implant as set forth in claim 26 wherein said sealing in said inert reactive atmosphere is produced by first flushing said package with a gas selected from the group consisting of nitrogen, helium, argon and neon and a combination thereof, followed by applying a vacuum of less than 3 inches of mercury to said package, followed by flushing said package with a gas selected from said group and a combination thereof.

30. The method for producing an implant as set forth in claim 25 wherein the olefin material is ultra high molecular weight polyethylene having a molecular weight between 400,000 and 10,000,000.

31. A method for producing a medical implant formed from an olefinic material comprising the steps of:
forming the implant from an olefinic material having a molecular weight of 400,000 to 10,000,000;
sealing the formed implant in an oxygen impermeable package in a substantially oxygen-free atmosphere;
radiation sterilizing said packaged implant; and
heating said sealed package implant for a predetermined time and temperature sufficient to form cross-links between free radicals in neighboring polymeric chains.

32. The method for producing an implant as set forth in claim 31 wherein said atmosphere contains less than 1% oxygen.

33. The method for producing an implant as set forth in claim 32 wherein said substantially oxygen free atmosphere is made up of a gas selected from the group consisting of nitrogen, helium, argon, and neon and a combination thereof.

34. The method for producing an implant as set forth in claim 32 wherein said substantially oxygen free atmosphere is produced by placing deoxidizing agents in said package prior to sealing.

35. The method for producing an implant as set forth in claim 32 wherein the polymeric material is ultra high molecular weight polyethylene.

36. A method for producing a sterile polymeric medical implant having improved oxidation resistance comprising the steps of:
sealing a polymeric medical implant in an oxygen-free atmosphere contained in a container comprising an oxygen impermeable composition;
sterilizing said implant by irradiation; and
heating said package and implant at a sufficient temperature and for a sufficient time to inactivate any residual free radicals and/or free radical precursors.

37. The method of claim 36 wherein said implant is formed from a polymeric article which has been freed of occluded oxygen gas.

38. The method of claim 36 wherein said free radical precursors include peroxy and hydroperoxy groups on the polymer chains.

39. The method of claim 36 wherein said oxygen free atmosphere comprises an inert gas or a vacuum.

40. The method of claim 39 wherein said inert gas contains no more than 1% oxygen.

41. The method of claim 39 wherein said atmosphere comprises a vacuum of not more than 3 inches of Mercury.

* * * * *